United States Patent [19]

Nodiff et al.

[11] 4,155,874
[45] May 22, 1979

[54] PHENOTHIAZINYL SULFIDES

[75] Inventors: Edward A. Nodiff, Philadelphia; Abraham Cantor, Elkins Park, both of Pa.

[73] Assignee: West Laboratories, Inc., Long Island City, N.Y.

[21] Appl. No.: 820,002

[22] Filed: Jul. 28, 1977

[51] Int. Cl.$^2$ ............................................. C07D 279/20
[52] U.S. Cl. ............................................. 252/402; 544/35; 544/41; 544/44; 424/246; 429/33; 429/191; 429/213
[58] Field of Search ............................ 544/35, 41, 44; 252/402

[56] References Cited
U.S. PATENT DOCUMENTS 2,659,724  11/1953  Zerbe ................................ 260/791

OTHER PUBLICATIONS

Nodiff et al., Chemistry and Industry, pp. 653–654, Aug. 7, 1976.
Chemical Abstracts, Eighth Collective Index, Subject Index, p. 23213S.
Lloyd E. Smith, Ind. Eng. Chem., Anal. Ed., vol. 10, p. 60, (1938).

Primary Examiner—John D. Randolph
Attorney, Agent, or Firm—Howard E. Thompson, Jr.

[57] ABSTRACT

A new group of compounds, generically classed as phenothiazinyl sulfides, are described having the formula:

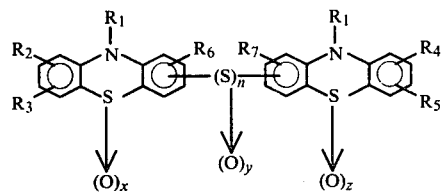

wherein n is 1 or 2, x and/or y and/or z represent 0, 1 or 2; $R_1$ may be H, alkyl, aryl, alkaryl, acyl, haloacyl and biologically activating aminoalkyl groups known in the medicinal arts, such as —$(CH_2)_3$—$N(CH_3)_2$,

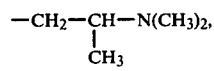

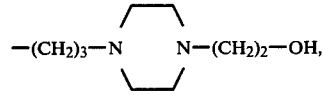

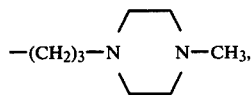

and -[2-(1-methyl-2-piperidyl)ethyl]; and $R_2$ and/or $R_3$ and/or $R_4$ and/or $R_5$ and/or $R_6$ and/or $R_7$ represent H, OH, Cl, Br, F, $CF_3$, SH, $NO_2$, CN, COOH, alkyl, alkoxy, sulfamoyl, dimethylsulfamoyl, dimethyl amino, aryl, alkaryl, acyl, aryloxy, methyl sulfonyl, methyl thio, and -S-phenothiazinyl substitutents; and as charge-transfer complexes of iodine therewith in which the number of moles of iodine associated with the molecule equals 1.5 (range 0.75 to 3.0) times the number of phenothiazinyl groups in the molecule.

Methods for the preparation of the compounds are described. The phenothiazinyl sulfides appear to be active in the same industrial and biological applications as phenothiazine and its corresponding derivatives, and show distinctive activity in various uses and as charge-transfer complexes of novel electrochemical properties as illustrated, in-vitro, in combination with iodine as a cathode material.

33 Claims, 1 Drawing Figure

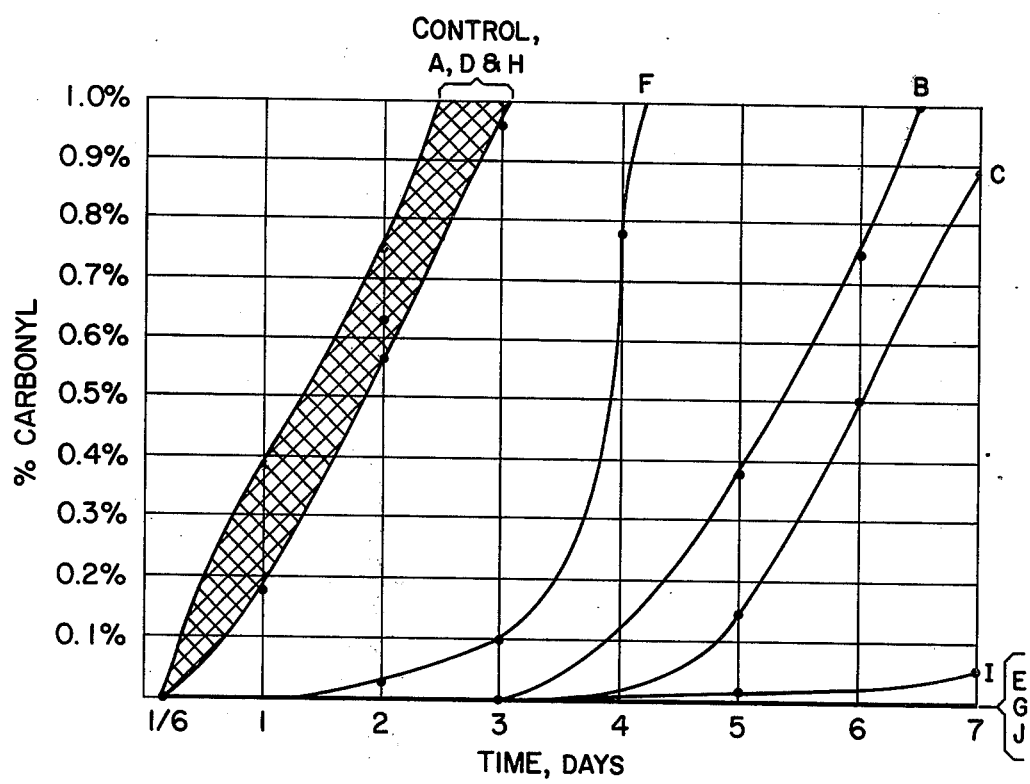

PHENOTHIAZINYL SULFIDES

This invention relates to a new group of compounds, generically classed as phenothiazinyl sulfides, in which phenothiazine moieties may be joined at the ring-bridging positions by a single or double sulfur bridge providing, for example, the monosulfide and the disulfide.

Methods for producing 3,3' phenothiazinyl monosulfide and disulfide were first disclosed in our publication, made jointly with others in "Chemistry and Industry", Aug. 7, 1976, under the title "Identification of the by-products in commercial phenothiazine.I. 3,3'-phenothiazinyl monosulphide". As pointed out in said publication, which is incorporated herein by reference, intensive investigation of the by-product fraction found in commercial phenothiazine production resulted in isolation of a component the infrared analysis of which suggested the possibility of a structure comprising several phenothiazine molecules connected by a sulfur bridge. Based on this lead, attempts to synthesize polyphenothiazinyl sulfides by different routes, more fully described in Examples 1 and 2 hereof, resulted in the preparation of phenothiazinyl monosulfide and disulfide and confirmed the fact that the sulfide bridge was at the 3,3' position. These syntheses also confirmed the fact that the component which had been isolated from the phenothiazine by-product residue was the 3,3' monosulfide.

The 3,3' phenothiazinyl sulfide and disulfide appear to exhibit the general properties and reactivity of phenothiazine. This has prompted the production of a number of derivatives of the sulfide and disulfide corresponding with the known industrially and biologically useful derivatives of phenothiazine. In general, derivatives which contain ring substituents can be produced by starting with the ring substituted phenothiazine and producing the substituted mono or disulfide by the same procedure used in producing the unsubstituted sulfide. On the other hand, for derivatives involving substitutions at the nitrogen, or the 10 position of the phenothiazine moiety, it is generally preferred to first form the mono or disulfide and then make the desired substitutions in the 10,10' positions. The unsubstituted sulfide and disulfide have a markedly reduced solubility as compared with phenothiazine.

The phenothiazinyl sulfides and derivatives thereof embraced by the present invention can be represented by the following formula:

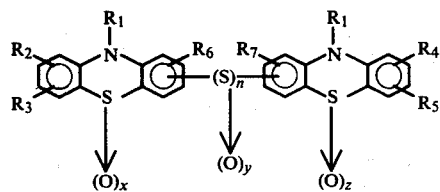

wherein n is 1 or 2, x and/or y and/or z represent 0, 1 or 2; $R_1$ may be H, alkyl, aryl, alkaryl, acyl, haloacyl and biologically activating aminoalkyl groups known in the medicinal arts, such as $-(CH_2)_3-N(CH_3)_2$,

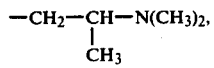

-continued

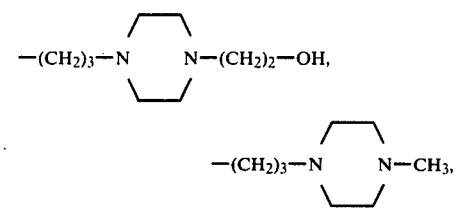

and -[2-(1-methyl-2-piperidyl)ethyl]; and $R_2$ and/or $R_3$ and/or $R_4$ and/or $R_5$ and/or $R_6$ and/or $R_7$ represent H, OH, Cl, Br, F, $CF_3$, SH, $NO_2$, CN, COOH, alkyl, alkoxy, sulfamoyl, dimethylsulfamoyl, dimethyl amino, aryl, alkaryl, acyl, aryloxy, methyl sulfonyl, methyl thio, and -S-phenothiazinyl substitutents; and as charge-transfer complexes of iodine therewith as illustrated, in-vitro, by complexes having unique electrochemical properties when, for example, the number of moles of iodine associated with the molecule equals 1.5 (range 0.75 to 3.0) times the number of phenothiazinyl groups in the molecule.

In the foregoing formula it is apparent that terms such as "aryl, alkaryl, aryloxy, acyl and haloacyl" have meanings which embrace typical phenothiazine substituents such as "phenyl, benzyl, phenoxy, acetyl and haloacetyl" respectively. As is apparent from the literature, the electron activities or charge-transfer complex formations of polycyclic compounds such as phenothiazine are subject to manipulation, by the inclusion of one or more of the substituents described above, to modify the compound properties. For example, the introduction of electron donating groups such as dimethyl amino would provide molecules which could be the basis for dyes and stains similar to methylene blue. However, the major activating groups cited as substituents often have an electron withdrawing effect, as in the derivative drug compounds of phenothiazine itself; for those compounds it has been proposed that charge-transfer complex formation, as electrodes at the surface of biological membranes, is functional in their in-vivo activities ("The Phenothiazines and Structurally Related Drugs", ed. by I. S. Forrest, C. J. Carr and E. Usdin, 1974: F. Gutman, et al, p. 30 and Szent-Gyorgi, cited by J. J. H. McDowell, p. 33).

The hereinafter described unique in-vitro electrochemical activity of the unsubstituted phenothiazinyl sulfides, in charge-transfer complexes, is therefore suggestive of unique invivo activity for the derivatives of those compounds, as compared with the familiar biological activities of the derivatives of phenothiazine itself.

The new 3,3' phenothiazinyl sulfides and disulfides form charge-transfer complexes with iodine and other halogens. The use of complexes of iodine with phenothiazine and its derivatives has been reported in the recent literature, as for example in U.S. Pat. Nos. 3,438,813 issued Apr. 15, 1969, to S. M. Davis and assigned to American Cyanamid Company; 3,653,968 issued Apr. 4, 1972, to D. V. Louzes and assigned to Union Carbide Corporation; 3,660,163 issued May 2, 1972, to J. R. Moser and assigned to Catalyst Research Corporation; and 3,660,164 issued May 2, 1972, to Hermann, Gutmann and Rembaum and assigned to California Institute Research Foundation; and in publications by F. Gutmann and H. Keyser in "Journal of Chemical Physics", Vol. 50 (1), pages 550-51 (1962) entitled "Electromeasurements on Phenothiazine Bases"; by M. Pampallona et al in "Journal of Applied Electrochemistry", Vol. 6 (3), pages 269–274 (1976) entitled "A Study of Some Charge Transfer Complexes as Electrodes in Solid State Cells"; by Yoshio Matsunaga in "Helvetica Physica Acta", Vol. 36 (6), pages 800–802 (1963) entitled "Some New Organic Semiconductors: Thiazine-Iodine Complexes"; and by Gutman and Keyser in "Journal of Chemical Physics", Vol. 46 (5), pages 1969–1974 (March 1967) entitled "Study of Phenothiazine- and Chlorpromazine-Iodine Complexes".

Whereas phenothiazine and its derivatives were reported to complex with iodine ($I_2$) in molar ratios ranging from about 1—1 to 1—2, with the optimum being about 1-1.5, the 3,3' phenothiazinyl sulfides and disulfides complex with iodine in molar ratios of about 1-1.5 to 1-6, with the optimum being about 1-3. This increase in the molar ratio of complexed iodine has been found to have a markedly advantageous effect on the electrical properties such as are critical for cathode material in solid state electrochemical cells.

The above mentioned U.S. Pat. Nos. 3,653,968 and 3,660,164 are of special interest in clearly pointing out how polycyclic compounds, including sulfur and nitrogen containing heterocyclic compounds such as phenothiazine, are effective donor components with a halogen such as bromine, and especially iodine, as the acceptor component and provide charge-transfer complexes useful as cathode material in solid state electrochemical cells. As pointed out in U.S. Pat. No. 3,653,968 the cathode material may be powdered and compressed alone or blended prior to compressing with solid state electrolyte and carbon in the form of graphite and acetylene black.

U.S. Pat. No. 3,660,164 also stresses the significance of resistivity in a cathode composition comprising a charge-transfer complex in which the polycyclic compound is the donor and bromine or iodine is the acceptor. It is in this area, as more clearly brought out in Example 12, that the 3,3' phenothiazinyl sulfides appear to be distinctly superior since preliminary testing has indicated their resistivity to be only about one-tenth that of a corresponding phenothiazine compound.

Recognizing that this advantage over phenothiazine may be the result of an intrinsic difference in the steric or molecular packing characteristic of the phenothiazinyl sulfide when complexed with iodine, it is suggested that those polymeric phenothiazinyl sulfide forms containing x phenothiazine moieties and x-1 sulfur bridges, where x=3 or more, will provide progressively greater reduction in resisitivity of the iodine complexes. In such polymeric complexes the number of moles of iodine will be 0.75x to 3.0x, and generally about 1.5x, having reference to the above definition of x.

Complexes of iodine with the 3,3' phenothiazinyl compounds can be prepared in various ways such as by dry grinding together of the sulfide and elemental iodine or by combining the sulfide and iodine in a suitable solvent medium and evaporating the solvent to leave a powdered complex. The complex produced by the solvent method appears thus far to be superior to the dry-blended complex, but the solvent method presents a problem due to the limited solubility of the 3,3' phenothiazinyl sulfides in some solvents. Various solvents are suitable for forming iodine complexes with 3,3' phenothiazinyl sulfides, including acetonitrile and methylene chloride. With sulfides having solubilizing substituents other solvents may also be appropriate. Methods of preparation of the complexes and the criticality of the role of the Phenothiazine-Iodine ratios are also elaborated by Susumu Doi et al in "Bulletin of the Chemical Society of Japan", Vol. 50 (4), pages 837–841 (1977) entitled "Electrical Properties and Constitution of the Phenothiazine-Iodine and Related Complexes".

The new phenothiazinyl sulfides and disulfides are also useful as antioxidants, stabilizers and inhibitors in certain of the industrial chemical systems in which phenothiazine and its derivatives have been used. As pointed out in U.S. Pat. No. 2,786,080 polyoxyalkylene compounds are a valuable and well-known class of organic compounds that are used as synthetic lubricants, hydraulic fluids, detergents, plasticizers and in other diverse applications. They have the shortcoming, however, of being highly susceptible to oxidation, particularly at elevated temperatures. Oxidation of these compounds produces strongly odoriferous products which are objectionable in many compositions. Such oxidation attack is particularly objectionable when the polyoxyalkylene compounds are employed as lubricants, since the resulting oxidation products are highly corrosive in nature, and adversely change the viscosity characteristics of the lubricant.

Practical evaluations which have been conducted to date indicate that the 3,3' phenothiazinyl sulfides and disulfides do exhibit antioxidant activity equal to or greater than the corresponding phenothiazine compound. Such advantage in some systems may be partly offset by a reduced solubility for the sulfides, unless alkylated to increase the solubility. In certain organic systems where phenothiazine and its derivatives have been used an antioxidants, however, the 3,3' phenothiazinyl sulfides have been found to be more active than phenothiazine itself, as illustrated herein by the stabilization of a polyoxyalkylene compound against oxidation. The methodology described below involved minor changes from that described in U.S. Pat. No. 2,786,080, which patent reported the efficacy of phenothiazine itself, as compared with various other antioxidants, in the stabilization of a polyoxyalkalene compound against oxidation. As more fully described in Example 11, hereinafter appearing, a comparison of the activities of BHT (butylated hydroxytoluene), phenothiazine (WLZ-11), phenothiazinyl monosulfide (WLZ-53), and phenothiazinyl disulfide (WLZ-54), as against a "control" sample containing no antioxidant additive, indicates the different type of activity of phenothiazine derivatives from conventional antioxidants such as BHT, and illustrates the significantly greater antioxidant effectiveness of the phenothiazinyl sulfides than phenothiazine itself. As between the monosulfide and disulfide, the phenothiazinyl monosulfide appears to provide the greater antioxidant activity.

The preparation of sulfoxide and sulfone derivatives of the 3,3' phenothiazinyl sulfides may be effected by reacting the same with hydrogen peroxide in a suitable solvent such as glacial acetic acid, as more fully pointed out in Example 9.

The following examples will serve to illustrate how 3,3' phenothiazinyl sulfide and disulfide and typical derivatives thereof and iodine complexes therewith can be prepared. In these examples it is to be understood that melting points were determined in capillary tubes in an electrically heated Thiele-Dennis apparatus and are uncorrected. Elemental analyses were performed by Micro-Analysis, Inc., Wilmington, Delaware. Infrared spectra were taken as Nujol mulls on a Perkin-Elmer Model 137B Infracord Spectrophotometer. Thin-layer chromatography of heavily loaded spots was carried out on Eastman Chromatogram sheets, type 6060 (silica gel with fluorescent indicator) using acetone or DMF as spotting solvents and freshly distilled ether as the developing solvent. The thin-layer chromatograms could be examined immediately under long and short ultraviolet light but best visualization was provided by long exposure (48h) to air and white light. All temperatures are reported in ° C.

EXAMPLE 1 phenothiazine $\xrightarrow{S, I_2}$ 3,3'-phenothiazinyl monosulfide

A stirred mixture of distilled phenothiazine (120 g, 0.6 mole), sublimed sulphur (9.6 g, 0.3 mole) and 0.6 g of iodine (0.5 percent wt on phenothiazine) was maintained at 190° C. for 70 min. ($H_2S$ evolution was essentially complete after 40 min.). On cooling, the mixture solidified to a hard green-brown cake (122 g, mp 189°–194° C.) whose removal necessitated cracking of the reaction flask. Soxhlet-extraction of a 100 g aliquot of the finely crushed cake, with freshly distilled ether, for 85 h, left 15 g of a green ether-insoluble residue which decomposed ca 275° C. Crystallisation of a 2 g aliquot of this residue from aniline followed by washing with hot benzene provided 1.2 g of 3,3' phenothiazinyl monosulfide as a yellow solid which decomposed ca 290° C. An analytical sample was prepared by dissolving the aniline-crystallised material in room temperature DMF, treating with carbon, filtering and concentrating the filtrate under reduced pressure. The resulting solid, after washing with hot benzene and drying for 6 h at 150° C. and 0.4 mm, decomposed ca 290° C.

Analysis calculated for $C_{24}H_{16}N_2S_3$: C, 67.25; H, 3.77; S, 22.44, Found: C, 67.08, H, 3.81; S, 22.61.

The infrared spectrum of this solid shows infrared peaks at the following wavelengths ($\mu$): 3.0, 6.3, 6.4, 7.05, 7.7, 7.8, 7.9, 8.05, 8.7, 8.9, 9.05, 9.7, 10.85, 11.4, 11.7, 12.2, 12.45, 13.15 (sh), 13.3, 13.6, 14.05, 14.15, 14.6, 14.95.

This infrared spectrum is identical with that of a byproduct impurity isolated from commercial phenothiazine, about 95 percent pure, by the following procedure:

A quantity of a commercial phenothiazine was sublimed, in a Kontes vacuum sublimator (Cat. No. K85550, 30×75 mm size), at 105° C. and 0.1 mm for 14 h. The resulting orange-black forerun (<0.5 percent wt) was removed from the condenser, and sublimation was contained for another 16 h at 145° C. and 0.1 mm to remove the main phenothiazine fraction. Nothing more sublimed from the residue after an additional 14 h at the same temperature and pressure. The sublimation residue was a dark green, amorphous, phenothiazine-free (t.l.c.) solid which decomposed ca 245° C. and amounted to 3–5 percent wt. Soxhlet-extraction of the sublimation residue with ether, for 48 h, left its major component as an ether-insoluble solid. Crystallisation of this material from aniline, washing with hot benzene and vacuum drying provided a dark green solid which decomposed at ca 280° C., and showed the infrared spectrum above noted.

EXAMPLE 2

3-mercaptophenothiazine $\xrightarrow{air}$ 3,3'-phenothiazinyl disulfide $\xrightarrow{\Delta}$ 3,3'-phenothiazinyl monosulfide A quantity of 3-mercaptophenothiazine was prepared by alkaline hydrolysis of phenothiazine-3-isothiuronium chloride as described by Daneke, J. and Wanzlick, H. W. Ann. 1970, 740, 52, and a 2 g portion thereof was suspended in 400 ml of boiling water. A stream of air was passed, for 5 h, through the vigorously stirred suspension to give 1.9 g of 3,3'-phenothiazinyl disulfide. The almost-pure reaction product was dissolved in acetone, at room temperature, treated with carbon and concentrated. The resulting yellow solid was vacuum-dried at 140° C. and 0.4 mm to give the analytical sample which decomposed ca 280° C.

Analysis calculated for $C_{24}H_{16}N_2S_4$: C, 62.57; H, 3.50; S, 27.84, Found: C, 62.65; H, 3.54; S, 27.72.

The infrared peaks for 3,3'-phenothiazinyl disulfide are at the following wavelengths ($\mu$): 3.0, 6.3, 6.45, 7.05, 7.7, 7.8, 7.9, 8.05, 8.15, 8.65, 8.75, 8.9, 9.1, 9.3, 9.7, 10.7, 10.8, 11.2, 11.25, (sh), 11.7, 11.8, 11.9, 12.25, 12.35, 13.4, 13.55 (sh), 14.1, 14.6.

A 0.2 g sample of the disulfide was maintained at 255° C. and 0.1 mm for 2 h. Some sublimation occurred leaving a residue of 3,3'-phenothiazinyl monosulfide whose infrared spectrum was identical with that of the material isolated in Example 1.

It should be noted that the identity of infrared spectra for the products of Examples 1 and 2 provides confirmation that the sulfur bridge of the Example 1 product is at the 3,3' location. The method of Example 1 would be the method of choice for producing moderate quantities of 3,3'-phenothiazinylmonosulfide. The method of Example 2 provides better yields, however, and for larger quantity production of the monosulfide this could be the method of choice.

EXAMPLE 3

2,2'-Dichloro-7,7'-phenothiazinyl monosulfide

A mechanically stirred mixture of 23.4 g (0.10 mole) of 2-chlorophenothiazine, 1.6 g (0.05 mole) of sublimed sulfur and 0.12 g (0.5 wt % on 2-chlorophenothiazine) of iodine, in a 100 ml round-bottom flask, was lowered into an oil bath preheated to 235°. The mixture was maintained at 220° for one hour although $H_2S$ evolution was essentially complete in about 45 minutes. The mixture, which consisted of a dark brown liquid containing pale green solid particles, was allowed to cool to room temperature. The resulting hard solid was removed from the flask and ground to a fine green powder with a mortar and pestle; wt of powder 22.6 g; mp 167°–250°. The powder was extracted with $Et_2O$, for 23 hours, in a soxhlet apparatus (during this time the solid was periodically removed from the thimble and re-pulverized. At the end of 3 hr, it weighed 11.4 g and melted 284°–291°. After 23 hr, it weighed 4 g and melted 331°–333°). Two crystallizations from aniline (25 ml each time) provided an analytical sample of 2,2'-dichloro-7,7'-phenolthiazinyl monosulfide as pale green plates, mp <350°.

Analysis calculated for $C_{24}H_{14}Cl_2N_2S_3$: C, 57.90; H, 2.84; Cl, 14.25; S, 19.34. Found: C, 58.18, H, 281; Cl, 13.98; S, 19.08.

The general procedure described in the foregoing example can be utilized in preparing other ring-substituted phenothiazinyl sulfides embraced by the formula earlier presented by selecting as starting materials phenothiazine containing the desired ring substituents.

EXAMPLE 4

Chlorpromazine 7,7'-Monosulfide Dipicrate

Into a 500 ml 4-neck, round-bottom flask equipped with a mechanical stirrer, reflux condenser, thermometer and nitrogen inlet were placed 5.0 g (0.01 mole) of 2,2'-dichloro-7,7'-phenothiazinyl monosulfide and 150 ml of DMSO. To this stirred suspension, at room temperature, was added 1.1 g (0.022 mole) of sodium hydride (50% dispersion in oil) in a single portion. Within minutes, there was a color change from green-white to orange to red accompanied by gentle effervescence. The mixture was heated up to 100° (internal) during 25 min, maintained at 100° for 1 hr. and allowed to cool to room temperature. To the red mixture, at room temperature, was added, in a single portion, a solution of 3.80 g (0.03 mole) of 3-dimethylaminopropyl chloride (DMPC) in 50 ml of DMSO. The red-brown mixture was heated to 115° during 15 min. and kept at 115° for 4 hr. The resulting dark brown mixture was cooled to room temperature and poured into 1 liter of cold $H_2O$, containing 1 g of $NH_4Cl$, to give an off-white suspension. The suspension was extracted with $CHCl_3$ (3×250 ml) and the orange extract was extracted with 10% HCl (5×200 ml) and $H_2O$ (1×200 ml). The acid and $H_2O$ extracts were combined and basified, with 10% NaOH, with cooling, to pH 10. The resulting suspension was extracted with $CHCl_3$ (3×150 ml) and the extract was dried ($Na_2SO_4$) and concentrated in vacuo to leave 1 g of yellow-brown oil. Attempts to convert this oil to hydrochloride, hydrobromide, phosphate, maleate and citrate salts were unsuccessful. The remaining oil (0.8 g) was dissolved in 50 ml of EtOH and treated with a solution of 1 g of picric acid in 50 ml of EtOH. The orange picrate (crude wt, 1.1 g) was washed with several 20 ml portions of cold EtOH, dissolved in 100 ml of boiling acetone, treated with carbon and filtered. The filtrate was slowly diluted with $Et_2O$ until a small amount of sticky orange solid separated. This material was discarded and the decantate was then further diluted with $Et_2O$ to 800 ml precipitating 0.6 g of chlorpromazine 7,7'-monosulfide dipicrate as a bright yellow solid. Two additional crystallizations from a mixture of 50 ml of acetone and 400 ml of $Et_2O$ gave the analytical sample which shrank and darkened at 116°-118° and melted with decomposition at 134°-136°. The analytical sample was dried for 4 hr. at 60° and 0.2 mm.

Analysis calculated for $C_{46}H_{42}Cl_2N_{10}O_{14}S_3$: C, 49.06; H, 3.76; Cl, 6.29; O, 19.89; S, 8.54. Found: C, 49.17; H, 3.99; Cl, 6.21; O, 20.12; S, 8.58.

EXAMPLE 5

Promazine 3,3'-Monosulfide Dipicrate

Into a one-liter, 4-neck, round-bottom flask equipped with a mechanical stirrer, reflux condenser, thermometer and nitrogen inlet were placed 8.6 g (0.02 mole) of 3,3'-phenothiazinyl monosulfide prepared as described in Example 1, and 200 ml of DMSO. To this solution, at room temperature, was added 2.15 g (0.044 mole) of sodium hydride (50% dispersion in oil) in a single portion. Immediate effervescence and a color change to red were observed. The mixture was stirred under $N_2$ at 100° for 1 hr, cooled to room temperature and treated, in a single portion, with a solution of 7.32 g (0.06 mole) of DMPC in 100 ml of DMSO. The mixture, which immediately turned brown, was stirred under $N_2$ for 4 hr. at 110°-120° and allowed to stand at room temperature overnight. On pouring into a solution of 1.5 g of $NH_4Cl$ in 2 liters of $H_2O$, a suspension formed which was extracted with $CHCl_3$ (7×500 ml). The combined $CHCl_3$ extracts were extracted with 5% HCl (10×250 ml) and the acidic extract was basified, with cooling, to pH 11 with 10% NaOH. The resulting suspension was extracted with $CHCl_3$ (6×300 ml) and the extract was washed with one liter of $H_2O$ and dried overnight ($Na_2SO_4$). Filtration and evaporation under reduced pressure left 10 g of viscous brown oil. An aliquot (5 g) of the oil in 100 ml of EtOH was converted to its picrate with ethanolic picric acid. The crude picrate (3.5 g) was extracted with 90 ml of acetone (insoluble brown tar discarded) and the extract was treated with carbon and diluted with 800 ml of $Et_2O$ to give 1.5 g of promazine 3,3'-monosulfide dipicrate. An additional crystallization from acetone-ether provided 1.1 g of the purified product; mp 138°-143°, after drying for 4 hr. at 60° and 0.1 mm.

Analysis calculated for $C_{46}H_{44}N_{10}O_{14}S_3$: C, 52.26; H, 4.19; O, 21.19; S, 9.10. Found: C, 52.00; H, 4.19; O, 20.97; S, 9.09.

The procedure of the foregoing example can be utilized with known variations in preparing other N-substituted phenothiazinyl sulfides embraced by the formula earlier presented by substituting the appropriate side chain materials for the DMPC.

EXAMPLE 6

10,10'-Dimethyl-3,3'-phenothiazinyl monosulfide

Into a 500 ml, 4-neck round-bottom flask equipped with a mechanical stirrer, reflux condenser, thermometer and addition funnel were placed, under a nitrogen blanket, 12.9 g (0.03 mole) of crude 3,3' phenothiazinyl monosulfide and 300 ml of DMSO. A 50% dispersion of sodium hydride in mineral oil (3.3 g, 0.07 mole) was added in a single portion, and the mixture was stirred for 1 hr at 40°-50° and allowed to cool to room temperature. Through the addition funnel was added, dropwise, 25.5 g (0.18 mole) of methyl iodide and the mixture was stirred at 40°-50° for 4 hr and at room temperature for 24 hr. The mixture was filtered and the filtrate was poured into 1.5 liters of $H_2O$ to give a solid which weighed 6.5 g after drying at 50°-60° and 0.1 mm for 3 hr. This material was extracted with 400 ml of benzene (insoluble tar discarded) and the extract was passed through a silica column. The column was eluted with an additional 1.5 liters of benzene and the combined eluates were treated with carbon, concentrated in vacuo to 400 ml and poured into 1 liter of ligroine (bp 90°-120°). A small amount of solid was filtered and the volume of the filtrate was reduced to 150 ml affording 10,10'-dimethyl-3,3'-phenothiazinyl monosulfide as a pale yellow solid; mp indefinite at about 140°. The weight, after drying at 50°-60° and 0.1 mm for 2 hr, was 2.5 g.

Analysis calculated for $C_{26}H_{20}N_2S_3$: C, 68.42; H, 4.38; N, 6.14. Found: C, 68.23; H, 4.23; N, 5.90.

EXAMPLE 7a

2-Chlorophenothiazine-7-isothiuronium chloride monohydrate

Into a three-neck, 3-liter, round-bottom flask equipped with a mechanical stirrer, reflux condenser, addition funnel and provisions for a nitrogen atmosphere, were placed 46.8 g (0.2 mole) of 2-chlorophenothiazine, 40 g (0.53 mole) of thiourea, 20 g (0.2 mole) of potassium acetate and 2 liters of absolute methanol. To this stirred mixture was added, from the addition funnel, during 30 minutes, at room temperature, 80 g (0.5 mole) of anhydrous ferric chloride in 300 ml of absolute methanol. Stirring was continued at room temperature for 24 hours and the mixture was filtered. The filtrate was poured into 3 liters of water and the resulting suspension was extracted with dichloromethane (4×700 ml) until the aqueous layer was clear. Saturation of the aqueous layer with NaCl provided a solid which was dried at 80°–100° and 0.4 mm for 4 hr; wt. 9.5 g. This material was extracted with 400 ml of boiling methanol and the extract was treated with carbon and diluted with 400 ml of Et$_2$O. Concentration in vacuo gave, after drying at 90°–100° and 0.4 mm for 6 hours, 7 g of 2-chlorophenothiazine-7-isothiuronium chloride monohydrate, mp 265°–266°.

Analysis calculated for $C_{13}H_{13}Cl_2ON_3S_2$: C, 44.31; H, 3.69; N, 11.93. Found: C, 44.64; H, 3.22; N, 11.95.

EXAMPLE 7b

2-Chloro-7-mercaptophenothiazine

A mixture of 7.04 (0.02 mole) of 2-chlorophenothiazine-7-isothiuronium chloride monohydrate and 100 ml of 6N NaOH (saturated with N$_2$ to remove air) was stirred under reflux, in a nitrogen atmosphere, for 24 hours. It was diluted with 250 ml of H$_2$O and acidified to pH 4 with 300 ml of 2N H$_2$SO$_4$. The resulting suspension was extracted with benzene (4×300 ml) leaving an aqueous layer in which was suspended 3.2 g of very crude 2,2'-dichloro-7,7'-phenothiazinyl disulfide. The benzene extract was dried (Na$_2$SO$_4$) and concentrated in vacuo to 50 ml to give 1.3 g of 2-chloro-7-mercaptophenothiazine. Recrystallization from benzene afforded an analytical sample of the mercaptan; mp 230°–232°.

Analysis calculated for $C_{12}H_8ClNS_2$: C, 54.23; H, 3.01; N, 5.27. Found: C, 54.43; H, 3.07; N, 5.33.

EXAMPLE 7c 2,2'-Dichloro-7,7'-phenothiazinyl disulfide

The crude 2,2'-dichloro-7,7'-phenothiazinyl disulfide (3.2 g) isolated in the synthesis of Example 7b above, was extracted with boiling acetone (2×750 ml) and the extract was concentrated under reduced pressure to give 0.75 g of purified disulfide; mp>300°. An additional crystallization from acetone gave the analytical sample.

Analysis calculated for $C_{24}H_{14}Cl_2N_2S_4$: C, 54.44; H, 2.64; S, 24.19. Found: C, 54.38; H, 2.74; S, 24.07.

Following the aeration procedure described in Example 2, the mercaptan produced in Example 7b can be converted to 2,2'-dichloro-7,7'-phenothiazinyl disulfide in good yield. This can in turn be converted to 2,2'-dichloro-7,7'-phenothiazinyl monsulfide by heating under vacuum as described in Example 2.

EXAMPLE 8

10,10'-Diacetyl-3,3'-phenothiazinyl monosulfide

A mixture of 8.6 g of 3,3'-phenothiazinyl monosulfide, 65 ml of acetic anhydride and 2 drops of pyridine was magnetically stirred, under reflux for 30 min. At this time, the initial suspension had turned to a dark solution. Reflux was continued for 3.5 hours and the solution was allowed to cool. It was poured into cold H$_2$O and the resulting sludge was stirred for 15 min. and allowed to stand overnight. The solid was collected, washed with Et$_2$O and pumped dry for 3 hours at 60°–70° and 0.2 mm. yielding 5.3 g of crude 10,10'-diacetyl-3,3'-phenothiazinyl monosulfide. The infrared spectrum of the unpurified material tends to confirm the above structure.

EXAMPLE 9

3,3'-phenothiazinyl monosulfide trisulfone

A mixture of 1.07 g of 3,3'-phenothiazinyl monosulfide and 25 ml of glacial acetic acid was warmed to 60°, allowed to cool to room temperature and treated with 15 ml of 30% H$_2$O$_2$. This mixture was heated at 90°–100° C. for 1.5 hours and the resulting yellow suspension was allowed to cool and filtered. The yellow solid was washed with water and dried in vacuo at 60°–80° C. for 2 hours to give 0.8 g of yellow solid; mp>300° C. Crystallization from DMF-EtOH and drying at 125°–130° C. and 0.1 mm for 4 hr gave a sample melting at>300° C. whose infrared spectrum suggests 3,3'-phenothiazinyl monosulfide trisulfone.

By reducing the amount of H$_2$O$_2$ in the foregoing reaction and appropriately adjusting the time and temperature of the reaction, it is believed possible to prepare mono-, di- and trisulfoxides as well as oxidized forms containing both sulfoxide and sulfone groups. Furthermore, when the starting material is a 3,3'-phenothiazinyl disulfide, oxidation to sulfoxide or sulfone can take place at both sulfur atoms of the sulfur bridge.

EXAMPLE 10

A comparison of the antioxidant activities of BHT (butylated hydroxytoluene), phenothiazine (WLZ-11), phenothiazinyl monosulfide (WLZ-53), and phenothiazinyl disulfide (WLZ-54), as against a "control" sample containing no antioxidant additive, was conducted according to the following procedure:

The testing was done in a 100° C. oven, with forced air circulation, in open 50.ml beakers. A 2.gram sample of the polyoxyalkylene compound (poloxamer 235) plus additive was added to each beaker. Replicate beaker samples were placed under test, for each test material, at each concentration of additive. Each beaker sample was a total analytical sample, thereby eliminating a change in specific surface such as is associated with removing analytical aliquots from a fixed volume sample. The high specific surface characterizing the 2.gram sample in a 50.ml beaker (i.e., specific surface equal to 5.25), taken together with the 100° C. exposure temperature, greatly accelerated the rate of oxidation of the sample, so that a seven-day exposure permitted meaningful determination of the relative induction periods prior to the initiation of active oxidation.

The results are summarized in the following table, and graphically illustrated in FIG. 1.

| ADDITIVE | | GRAPH LEGEND | PERCENT CARBONYL* MEASURED AFTER | | | | | | |
|---|---|---|---|---|---|---|---|---|---|
| | | | 1 HRS | 1 DAY | 2 DAY | 3 DAY | 4 DAY | 5 DAY | 6 DAY | 7 DAY |
| Control | | Control | <0.01 | 0.33 | 0.71 | 1.12 | 1.50 | 1.93 | 2.56 | 3.08 |
| BHT | 0.01% | A | — | — | 0.63 | 0.96 | 1.24 | 1.75 | 2.12 | 2.48 |
| | 0.05% | B | — | — | — | <0.01 | — | 0.38 | 0.75 | 1.21 |
| | 0.1% | C | — | — | — | 0.01 | — | 0.15 | 0.50 | 0.89 |
| WLZ-11: | 0.005% | D | — | 0.18 | 0.57 | 0.98 | 1.64 | 2.02 | 2.93 | 3.58 |

| ADDITIVE | GRAPH LEGEND | PERCENT CARBONYL* MEASURED AFTER | | | | | | | |
|---|---|---|---|---|---|---|---|---|---|
| | | 1 HRS | 1 DAY | 2 DAY | 3 DAY | 4 DAY | 5 DAY | 6 DAY | 7 DAY |
| Control | Control | <0.01 | 0.33 | 0.71 | 1.12 | 1.50 | 1.93 | 2.56 | 3.08 |
| 0.01% | E | — | — | — | 0.01 | — | 0.01 | 0.01 | 0.01 |
| WLZ-53: 0.005% | F | <0.01 | 0.01 | 0.03 | 0.01 | 0.78 | 1.37 | 2.93 | 4.18 |
| 0.01% | G | — | — | — | — | 0.01 | 0.01 | 0.01 | 0.01 |
| WLZ-54: 0.005% | H | 0.02 | 0.38 | 0.75 | 1.40 | 1.66 | 2.3 | 2.88 | 3.14 |
| 0.01% | I | — | — | — | <0.01 | — | — | — | 0.00 |
| 0.05% | J | — | — | — | 0.01 | — | — | 0.01 | 0.01 |

*Percent carbonyl determined from calibration curve using amyl acetate as source of the carbonyl group.

It will be apparent from the results in FIG. 1 that the phenothiazinyl monosulfide is exceptionally effective, in that it was the only additive characterized by a substantial extension in the induction period at a level of 0.005%. It will also be apparent from the graph of the tabulated results that the graph plotting was cut off at the 1.0 carbonyl level, above which value the data is of no primary relevance to the effect on induction period. Likewise, only samples E, G, and J were characterized by a full seven-day induction period (i.e., no carbonyl above the base level of 0.01%), under the test conditions. As a result, the activities of those additive levels were not differentiated.

EXAMPLE 11

As a preliminary step to preparing iodine complexes the solubilities in acetonitrile ($CH_3CN$) and in methylene chloride ($CH_2Cl_2$) were obtained for the following compounds:

A—phenothiazine
B—3,3'-phenothiazinyl monosulfide
C—3,3'-phenothiazinyl disulfide
D—10-methyl phenothiazine
E—10,10'-dimethyl phenothiazinyl monosulfide and the solubility data appears in the following table:

| Compound | Solvents | |
|---|---|---|
| | $CH_3CN$ | $CH_2Cl_2$ |
| A | Soluble | Soluble |
| B | Insoluble | Insoluble |
| C | Soluble | Slightly Soluble |
| D | Soluble | Soluble |
| E | Soluble | Soluble |
| Iodine Complexes of A to E* | Soluble | Soluble |

*As later determined.

In the case of insolubility or slight solubility the compounds were dispersed with ultrasonics for a sufficient time to complete the titration with iodine, for the determination of the stoichiometric equivalences.

Those titrations were conducted by the Wayne Kerr Bridge method using Gold electrodes, acetonitrile as solvent for the compound being tested, and at a temperature of 25° C. to determine the molar ratio of iodine complexing with the test compound. In these tests conductivities reached maxima at the optimum level of complex formation, and relevant data with respect to compounds A to E are presented in the following table.

| Compound | Molarity Compound in $CH_3CN$ | ($\times 10^{-4}$) Iodine in $CH_3CN$ | Maximum Conductance Occurs at Mole Fraction of Cpd | Ratio Cpd.:$I_2$ |
|---|---|---|---|---|
| A | 2.010 | 2.992 | 0.402 | 2:3 |
| B | 1.145 | 3.307 | 0.257 | 1:2.9 |
| C | 1.413 | 3.386 | 0.339 | 1:2.9 |
| D | 2.675 | 3.90 | 0.41 | 2:2.9 |
| E | 1.118 | 3.465 | 0.256 | 1:2.9 |

This data clearly demonstrates that iodine complexes with the 3,3'-phenothiazinyl compounds at the the Cpd:$I_2$ ratio of 1:3 rather than the 1:1.5 ratio which applies for phenothiazine and its derivatives.

Having established the complex stoichiometries, the solid state complexes for compounds A, B, and C were prepared from solution as follows: Each compound was dissolved in $CH_2Cl_2$, or dispersed in same ultrasonically where insoluble. The mixture was then heated to boiling on a steambath, and iodine solution in $CH_2Cl_2$ added dropwise to excess, yielding immediate green-black to brown-black solutions. The excess $CH_2Cl_2$ was evaporated almost to dryness, and remaining solvent removed under vacuum. The dry product was then washed with two small aliquots of hexane, and one small aliquot of pentane. These washes showed iodine color indicating that excess iodine was removed. The excess iodine initially added ranged from 0.5 to 3%.

The powders so prepared were compressed into pellets approximately 0.25 cm thick using approximately 3,000 kg/cm$^2$ pressure and the pellets were assembled with appropriate electrodes to measure resistivity according to the procedure described in the above mentioned Pampallona publication, "Journal of Applied Electrochemistry", Vol. 6 (3), pages 269–274. Complexes of iodine with compounds A, B and C were tested using graphite electrodes and provided good resistivity data as follows:

| Iodine Complex | Mole Ratio Cpd.:$I_2$ | Resistivity ohm-cm |
|---|---|---|
| A | 2:3 | 25.4 |
| B | 1:3 | 2.6 and 1.9 |
| C | 1:3 | 5.2 |

This data is considered to be of special significance. It indicates that both the 3,3'-phenothiazinyl monosulfide and disulfide form iodine complexes having a drastically lower resistivity than the phenothiazine-iodine complex, and that the benefit with the monosulfide is substantially greater than with the disulfide. The data also suggests that phenothiazinyl sulfide polymers containing three or more phenothiazine moieties might exhibit further drastic reduction of resistivity. The resistivity values for the complexes with compounds D and E, under the same conditions remain to be determined.

Various changes and modifications in the 3,3'-phenothiazinyl sulfides herein disclosed and the ways of utilizing the same as such or in the form of iodine complexes may occur to those skilled in the art, and to the extent that such changes and modifications are embraced by the appended claims it is to be understood that they constitute part of the present invention.

We claim:
1. An essentially pure poly-phenothiazinyl sulfide of the formula:

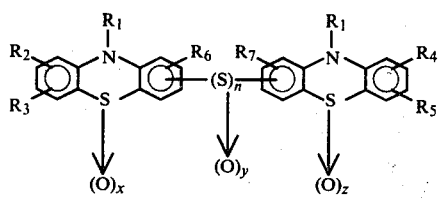

wherein n is 1 or 2, x and/or y and/or z represent 0, 1 or 2; $R_1$ represents H, alkyl, aryl, alkaryl, acyl, haloacyl and the biologically activating aminoalkyl groups known in the medicinal arts, —$(C_2)_3$—$N(CH_3)_2$,

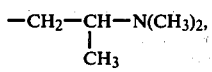

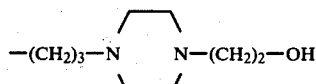

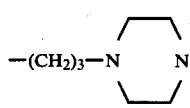

and -[2-(1-methyl-2-piperidyl)ethyl]; and $R_2$ and/or $R_3$ and/or $R_4$ and/or $R_5$ and/or $R_6$ and/or $R_7$ represent H, OH, Cl, Br, F, $CF_3$, SH, $NO_2$, CN, COOH, alkyl, alkoxy, sulfamoyl, dimethylsulfamoyl, dimethyl amino, aryl, alkaryl, acyl, aryloxy, methyl sulfonyl, methyl thio and S-phenothiazinyl substituents; and wherein the terms ayryl, alkaryl, aryloxy, acyl and haloacyl embrace typical phenothiazine substituents.

2. An essentially pure poly-phenothiazinyl sulfide as defined in claim 1, wherein phenothiazine moieties are joined by —S— bridges, and the phenothiazine moieties are otherwise unsubstituted.

3. An essentially pure poly-phenothiazinyl sulfide as defined in claim 2, in the form of 3,3'-phenothiazinyl monosulfide.

4. An essentially pure poly-phenothiazinyl sulfide as defined in claim 1, wherein phenothiazine moieties are joined by an —S—S— bridge, and the phenothiazine moieties are otherwise unsubstituted.

5. An essentially pure poly-phenothiazinyl sulfide as defined in claim 4, in the form of 3,3'-phenothiazinyl disulfide.

6. An essentially pure poly-phenothiazinyl sulfide as defined in claim 1, wherein each phenothiazine moiety contains at least one ring and/or N-substituent.

7. An essentially pure poly-phenothiazinyl sulfide as defined in claim 6, wherein said substituents are selected as providing an electron donating effect.

8. An essentially pure poly-phenothiazinyl sulfide as defined in claim 6, wherein said substituents are selected as providing an electron withdrawal effect.

9. An essentially pure poly-phenothiazinyl sulfide as defined in claim 6, wherein said substituents are selected as providing a solubility modifying effect.

10. An essentially pure poly-phenothiazinyl sulfide as defined in claim 6, wherein the phenothiazinyl moieties contain only ring substituents.

11. An essentially pure poly-phenothiazinyl sulfide according to claim 10 in the form of the 2,2'-dichloro-7,7'-monosulfide.

12. An essentially pure poly-phenothiazinyl sulfide according to claim 10 in the form of the 2,2'-dichloro-7,7'-disulfide.

13. An essentially pure poly-phenothiazinyl sulfide as defined in claim 6, wherein the phenothiazine moieties contain only N-substituents.

14. An essentially pure poly-phenothiazinyl sulfide according to claim 13 in the form of the 10,10'-dimethyl monosulfide.

15. An essentially pure poly-phenothiazinyl sulfide according to claim 13 in the form of promazine 3,3'-monosulfide.

16. An essentially pure poly-phenothiazinyl sulfide according to claim 13 in the form of the 10,10'-diacetyl monosulfide.

17. An essentially pure poly-phenothiazinyl sulfide as defined in claim 6, wherein the phenothiazinyl moieties contain both ring and N-substituents.

18. An essentially pure poly-phenothiazinyl sulfide according to claim 17 in the form of chlorpromazine 7,7'-monosulfide.

19. An essentially pure oxide derivative of a poly-phenothiazinyl sulfide as defined in claim 1.

20. An oxide essentially pure oxide derivative according to claim 19 in the form of an oxide derivative of 3,3'-phenothiazinyl monosulfide.

21. An essentially pure oxide derivative according to claim 19 in the form of the trisulfone derivative of 3,3'-phenothiazinyl monosulfide.

22. An iodine complex of an essentially pure poly-phenothiazinyl sulfide of the formula:

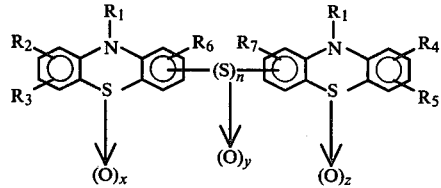

wherein n is 1 or 2, x and/or y and/or z represent 0, 1 or 2; $R_1$ represents H, alkyl, aryl, alkaryl, acyl, haloacyl and the biologically activating aminoalkyl groups known in the medicinal arts, —$(CH_2)_3$—$N(CH_3)_2$,

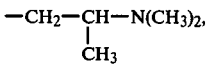

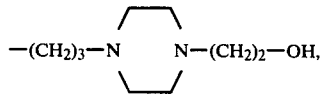

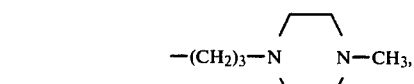

and -[2-(1-methyl-2-piperidyl)ethyl]; and $R_2$ and/or $R_3$ and/or $R_4$ and/or $R_5$ and/or $R_6$ and/or $R_7$ represent H, OH, Cl, Br, F, CF$_3$, SH, NO$_2$, CN, COOH, alkyl, alkoxy, sulfamoyl, dimethylsulfamoyl, dimethyl amino, aryl, alkaryl, acyl, aryloxy, methyl sulfonyl, methyl thio and —S— phenothiazinyl substituents; wherein the terms aryl, alkaryl, aryloxy, acyl and haloacyl embrace typical phenothiazine substituents; and wherein the number of moles of iodine associated with the molecule is about 1.5, and within the range of 0.75 to 3.0, times the number of phenothiazinyl groups in the molecule.

23. An iodine complex according to claim 22 in the form of 3,3'-phenothiazinyl monosulfide complexed with iodine in the molar ratio of 1:3.

24. An iodine complex according to claim 22 in the form of 3,3'-phenothiazinyl disulfide complexed with iodine in the molar ratio of 1:3.

25. An iodine complex according to claim 22 in the form of 10,10'-dimethyl phenothiazinyl monosulfide complexed with iodine in the molar ratio of 1:3.

26. A composition comprising an organic medium subject to oxidative deterioration having uniformly blended therewith a stabilizing amount within the general range of 0.005 to 0.05% by weight of an essentially pure poly-phenothiazinyl sulfide of the formula:

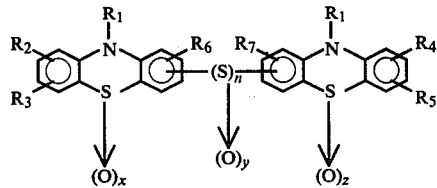

wherein n is 1 or 2, x and/or y and/or z represent 0, 1 or 2; R$_1$ represents H, alkyl, aryl, alkaryl, acylo, haloacyl and the biologically activating aminoalkyl groups known in the medicinal arts, —(CH$_2$)$_3$—N(CH$_3$)$_2$,

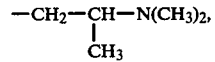

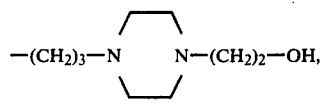

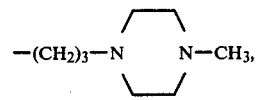

and -[2-(1-methyl-2-piperidyl)ethyl]; and R$_2$ and/or R$_3$ and/or R$_4$ and/or R$_5$ and/or R$_6$ and/or R$_7$ represent H, OH, Cl, Br, F, CF$_3$, SH, NO$_2$, CN, COOH, alkyl, alkoxy, sulfamoyl, dimethylsulfamoyl, dimethyl amino, aryl, alkaryl, acyl, aryloxy, methyl sulfonyl, methyl thio and —S-phenothiazinyl substituents; and wherein the terms aryl, alkaryl, aryloxy, acyl and haloacyl embrace typical phenothiazine substituents.

27. A composition according to claim 26, wherein the stabilizing agent is a poly-phenothiazinyl monosulfide.

28. A composition according to claim 27 wherein the organic medium is a polyoxyalkylene compound and the stabilizing agent is 3,3'-phenothiazinyl monosulfide in the amount of about 0.005 to 0.01% by weight.

29. A composition according to claim 26, wherein the stabilizing agent is a poly-phenothiazinyl disulfide.

30. A composition according to claim 29, wherein the organic medium is a polyoxyalkylene compound and the stabilizing agent is 3,3'-phenothiazinyl disulfide in the amount of about 0.01 to 0.05% by weight.

31. An essentially pure poly-phenothiazinyl sulfide according to claim 1, wherein the substituents aryl, alkaryl, aryloxy, acyl and haloacyl in said poly-phenothiazinyl sulfide, when present, are repectively phenyl, benzyl, phenoxy, acetyl and haloacetyl.

32. An iodine complex according to claim 22, wherein the substituents aryl, alkaryl, aryloxy, acyl and haloacyl in said poly-phenothiazinyl sulfide, when present, are respectively phenyl, benzyl, phenoxy, acetyl and haloacetyl.

33. A composition according to claim 26, wherein substituents aryl, alkaryl, aryloxy, acyl and haloacyl in said poly-phenothiazinyl sulfide, when present, are respectively phenyl, benzyl, phenoxy, acetyl and haloacetyl.

* * * * *